US008865173B2

(12) United States Patent
Spong et al.

(10) Patent No.: US 8,865,173 B2
(45) Date of Patent: Oct. 21, 2014

(54) TREATMENTS FOR PANCREATIC CANCER METASTASES

(75) Inventors: Suzanne M. Spong, San Francisco, CA (US); Thomas B. Neff, Atherton, CA (US); Stephen J. Klaus, San Francisco, CA (US)

(73) Assignee: Fibrogen, Inc., San Francisco, CA (US)

( * ) Notice: Subject to any disclaimer, the term of this patent is extended or adjusted under 35 U.S.C. 154(b) by 213 days.

(21) Appl. No.: 12/148,922

(22) Filed: Apr. 23, 2008

(65) Prior Publication Data

US 2008/0206256 A1 Aug. 28, 2008

Related U.S. Application Data

(63) Continuation of application No. 11/119,309, filed on Apr. 28, 2005, now abandoned.

(60) Provisional application No. 60/588,843, filed on Jul. 16, 2004, provisional application No. 60/566,277, filed on Apr. 28, 2004.

(51) Int. Cl.

| | |
|---|---|
| *A61K 39/395* | (2006.01) |
| *A61K 39/00* | (2006.01) |
| *C07K 14/71* | (2006.01) |
| *C07K 16/22* | (2006.01) |
| *A61K 45/06* | (2006.01) |
| *G01N 33/574* | (2006.01) |

(52) U.S. Cl.
CPC ......... *A61K 39/395* (2013.01); *A61K 39/39558* (2013.01); *C07K 14/71* (2013.01); *C07K 16/22* (2013.01); *G01N 2333/475* (2013.01); *A61K 2039/505* (2013.01); *A61K 45/06* (2013.01); *G01N 33/57438* (2013.01)
USPC .................. 424/141.1; 424/142.1; 424/145.1

(58) Field of Classification Search
None
See application file for complete search history.

(56) References Cited

U.S. PATENT DOCUMENTS

| | | | |
|---|---|---|---|
| 5,408,040 A | 4/1995 | Grotendorst et al. | |
| 6,562,618 B1 | 5/2003 | Tamatani et al. | |
| 7,384,634 B2 * | 6/2008 | Grotendorst et al. | |
| 7,405,274 B2 * | 7/2008 | Lin et al. | |
| 7,871,617 B2 * | 1/2011 | Lin et al. | 424/139.1 |
| 2005/0271670 A1 * | 12/2005 | Spong et al. | 424/155.1 |

FOREIGN PATENT DOCUMENTS

| | | |
|---|---|---|
| WO | WO 96/38172 A1 | 12/1996 |
| WO | WO 99/07407 A1 | 2/1999 |
| WO | WO-99/13910 A1 | 3/1999 |
| WO | WO 00/02450 A1 | 1/2000 |
| WO | WO 00/27868 A3 | 5/2000 |
| WO | WO 00/35936 A1 | 6/2000 |
| WO | WO 01/38532 A2 | 5/2001 |
| WO | WO 03/024308 A2 | 3/2003 |
| WO | WO 03/053340 A2 | 7/2003 |
| WO | WO 03/092584 A2 | 11/2003 |
| WO | WO 2004/108764 A2 | 12/2004 |

OTHER PUBLICATIONS

Fundamental Immunology. William E. Paul, M.D. ed., 3d ed., p. 242, 1993.*
Cardillo et al. International Journal of Cancer, 97(2):386-392, Jan. 20, 2002.*
Kryiazis et al. American Journal of Pathology, 106:250-260, 1982.*
Lieber et al. (Int. J. Cancer 1975 15(5):741-7).*
Kufe et al. (Cancer Medicine, 6th ed. from NCBI Bookshelf, 2003).*
Algul (2002) Int J Gastrointest Cancer 31:71-78.
Babic et al. (1999) Mol Cell Biol 19:2958-2966.
Bradham et al. (1991) J Cell Biol 114:1285-1294.
Brigstock (2002) Angiogenesis 5:153-165.
Croci et al. (2004) Cancer Res 64:1730-1736.
Denton and Abraham (2001) Curr Opin Rheumatol 13:505-511.
Franklin (1997) Int J Biochem Cell Biol 29:79-89.
Frazier et al. (1996) J Invest Dermatol 107:404-411.
Hishikawa et al. (1999) J Biol Chem 274:37461-37466.
Hoeflich et al. (2000) Nature 406:86-90.
Iacobuzio-Donahue et al. (2002) Am J Pathol 160:91-99.
Igarashi et al. (1998) J Cutan Pathol 25:143-148.
Ivkovic et al. (2003) Development 130:2779-2791.
Joliot et al. (1992) Mol Cell Biol 12:10-21.
Kang et al. (2003) Cancer Cell 3:537-549.
Kasaragod et al. (2001) Ped Dev Pathol 4:37-45.
Koliopanos et al. (2002) World J Surg 26:420-427.
Kondo et al. (2002) Carcinogenesis 23:769-776.
Kothapalli et al. (1997) Cell Growth Differ 8:61-68.
Matsuoka et al. (2002) Am J Physiol Lung Cell Mol Physiol 283:L103-L112.
O'Brien et al. (1990) Mol Cell Biol 10:3569-3577.
Pan et al. (2002) Neurol Res 24:677-683.
Pennica et al. (1998) Proc Natl Acad Sci U S A, 95:14717-14722.
Ricupero et al. (1999) Am J Physiol 277:L1165-1171.
Riewald (2001) Blood 97:3109-3116.
Ryseck et al. (1991) Cell Growth and Diff 2:225-233.
Shakunaga et al. (2000) Cancer 89:1466-1473.
Shimo et al. (1998) J Biochem (Tokyo) 124:130-140.
Shimo et al. (1999) J Biochem 126:137-145.
Shimo et al. (2001) Oncology 61:315-322.
Simmons et al. (1989) Proc. Natl. Acad. Sci. USA 86:1178-1182.
Uchio et al. (2004) Wound Repair Regen 12:60-66.
Vorwerk et al. (2000) Br J Cancer 83:756-760.
Wenger et al. (1999) Oncogene 18:1073-1080.
Wunderlich (2000) Graefes Arch Clin Exp Ophthalmol 238:910-915.
Xie et al. (2001) Cancer Res 61:8917-8923.
Xie et al. (2004) Clin Cancer Res 10:2072-2081.
Xu et al. (2004) J Biol Chem 279:23098-23103.
Yosimichi et al. (2001) Eur J Biochem 268:6058-6065.
Zhang et al. (1998) Mol Cell Biol 18:6131-6141.
Ryu, Byongwoo, et al., "Invasion-Specific Genes in Malignancy: Serial Analysis of Gene Expression Comparisons of Primary and Passaged Cancers," Cancer Research (2001) 61:1833-1838.
Weydert, Christine, et al., "Supression of the Malignant Phenotype in Human Pancreatic Cancer Cells by the Overexpression of Manganese Superoxide Dismutase," Mol. Cancer Therapeutics (2003) 2:361-369.

* cited by examiner

*Primary Examiner* — Peter J Reddig
(74) *Attorney, Agent, or Firm* — Fibrogen, Inc.

(57) ABSTRACT

The present invention provides methods for reducing tumor survival, expansion, and metastasis. In particular, the invention provides methods for reducing pancreatic tumor survival, expansion, and metastasis. The invention also provides agents for use in the methods, particularly agents that reduce the level or activity of connective tissue growth factor (CTGF), and methods for identifying such agents.

3 Claims, 9 Drawing Sheets

TREATMENTS FOR PANCREATIC CANCER METASTASES

This application is a continuation of U.S. application Ser. No. 11/119,309, filed 28 Apr. 2005, now abandoned, which claims the benefit of U.S. Provisional Application No. 60/588,843, filed 16 Jul. 2004 and U.S. Provisional Application Ser. No. 60/566,277, filed on 28 Apr. 2004, all of which are incorporated in their entirety by reference herein.

FIELD OF THE INVENTION

The present invention provides methods for reducing tumor survival, expansion, and metastasis. In particular, the invention provides methods for reducing pancreatic tumor survival, expansion, and metastasis. The invention also provides agents for use in the methods, particularly agents that reduce the level or activity of connective tissue growth factor (CTGF), and methods for identifying such agents.

BACKGROUND OF THE INVENTION

Cancer affects the lives of millions of people on a global basis. Treatments such as chemotherapy produce beneficial results in some malignancies, however, some cancers, including lung, pancreatic, prostate, and colon cancers, demonstrate poor response to such treatments. Further, even cancers initially responsive to chemotherapy can return after remission, with widespread metastatic spread leading to death of the patient. In addition, chemotherapy agents, e.g., antineoplastic agents, have significant toxicities, and are associated with side effects including, e.g., bone marrow suppression, renal dysfunction, stomatitis, enteritis, and hair loss. Therefore, there is a need for effective and safe therapies for treatment of cancer, prevention of metastasis, etc.

Connective Tissue Growth Factor (CTGF) is a growth factor with demonstrated effects in various physiological and pathological contexts, including mitogenic and chemotactic processes, and the production of extracellular matrix components. CTGF has been implicated in a number of disorders and conditions, including, but not limited to, disorders involving angiogenesis, fibrosis, and other conditions with proliferative aspects. CTGF has been previously identified as a critical factor associated with tumor formation and growth, and is overexpressed in a variety of tumor types. (See, e.g., International Publication No. WO 96/38172; Wenger et al. (1999) Oncogene 18:1073-1080; Xie et al. (2001) Cancer Res 61:8917-8923; Igarashi et al. (1998) J Cutan Pathol 25:143-148; Kasaragod et al. (2001) Ped Dev Pathol 4:3745; Shakunaga et al. (2000) Cancer 89:1466-1473; Vorwerk et al. (2000) Br J Cancer 83:756-760; Pan et al. (2002) Neurol Res 24(7):677-683.) CTGF is also known to have pro-angiogenic activity in vivo, an important process associated with tumor survival. (See, e.g., Brigstock (2002) Angiogenesis 5:153-165; Shimo et al. (1999) J Biochem 126:137-145; Babic et al. (1999) Mol Cell Biol 19:2958-2966; Ivkovic et al. (2003) Development 130:2779-2791; and Shimo et al. (2001) Oncology 61:315-322.)

However, correlation between CTGF expression and prognosis in cancer patients has suggested a context specific role for the protein. For example, CTGF expression was associated with longer patient survival in squamous cell carcinomas, but decreased survival in esophageal adenocarcinomas. (Koliopanos et al. (2002) World J Surg 26:420-427.) Similarly, CTGF has been implicated in increased apoptosis of, e.g., breast cancer cells, and increased survival of, e.g., rhabdomyosarcoma cells. (See, e.g., Hishikawa et al. (1999) J Biol Chem 274:37461-37466; Croci et al. (2004) Cancer Res 64:1730-1736.) Therefore, there is a need for improved understanding of cancer-associated CTGF-related effects, and for methodologies appropriately targeting CTGF within the context of the disease.

In summary, there is a need in the art for effective treatments for cancer, and, specifically, there is a need for methods of selective treatment that effectively targets CTGF-related or -induced aspects of cancer. The present invention meets these needs by providing methods for reducing tumor survival, expansion, and metastasis, and, in particular, by providing methods for reducing pancreatic tumor survival, expansion, and metastasis. The invention also provides agents for use in the methods, particularly reagents that reduce the level or activity of CTGF, and methods for identifying such agents.

SUMMARY OF THE INVENTION

In one embodiment, the present invention provides a method for identifying an agent that inhibits anchorage-independent cell growth, the method comprising (a) culturing MIA PaCa-2 cells, wherein the cells have been modified to express connective tissue growth factor (CTGF), with an agent under conditions suitable, in the absence of the agent, for anchorage-independent cell growth; (b) measuring the amount of cell growth that occurs in the presence of the agent; and (c) comparing the amount of cell growth that occurs in the presence of the agent with the amount of cell growth that occurs in the absence of the agent, wherein a decrease in the amount of cell growth in the presence of the agent relative to the amount of cell growth that occurs in the absence of the agent is indicative of an agent that inhibits anchorage-independent cell growth. In a certain embodiment, the CTGF is human CTGF. In another embodiment, the MIA PaCa-2 cells, when $10^5$ cells are cultured in a suitable growth medium, secrete into the culture medium at least about 0.3 µg CTGF/48 hrs.

In some embodiments, the measuring the amount of cell growth comprises counting clusters of cells. In a further embodiment, the culturing comprises dispersing the cells in a semi-solid support medium appropriate for anchorage-independent cell growth; and, in a specific embodiment, the semi-solid support medium comprises about 0.35% agar.

The present invention further encompasses various uses for agents that inhibit anchorage-independent cell growth identified by the above-described methods. In one aspect, the invention provides a method for reducing metastasis of a tumor in a subject, the method comprising administering to the subject an agent identified by any one of the above-described methods for identifying an agent that inhibits anchorage-independent cell growth, thereby reducing metastasis of the tumor in the subject. In a particular aspect, the tumor is a pancreatic tumor.

In another aspect, the invention provides a method for reducing expansion of a pancreatic tumor in a subject, the method comprising administering to the subject an agent identified by any one of the above-described methods for identifying an agent that inhibits anchorage-independent cell growth, thereby reducing pancreatic tumor expansion in the subject. In another aspect, the invention provides methods for reducing pancreatic tumor cell survival in a subject, the method comprising administering to the subject an agent identified by the above-described methods for identifying an agent that inhibits anchorage-independent cell growth, thereby reducing pancreatic tumor cell survival in the subject.

The invention further encompasses a method for reducing metastasis of a tumor in a subject, the method comprising administering to the subject an agent that inhibits CTGF activity, thereby reducing metastasis of the tumor. In a specific embodiment, the tumor is a pancreatic tumor. In preferred embodiments, the subject is a mammal, and, in a most preferred embodiment, a human. Whether an agent inhibits CTGF activity can be determined by any one of a number of methods well-known to those in the art, for example, using the anchorage-independent growth assay as described above (supra).

In one embodiment, the tumor is an adenocarcinoma, and, in a further embodiment, the tumor is a ductal adenocarcinoma.

In various embodiments, the agent is an oligonucleotide that specifically binds to a polynucleotide encoding CTGF; is a small molecule; or is an aptamer. In a preferred embodiment, the agent is an antibody that specifically binds to CTGF. In certain embodiments, the antibody that specifically binds to CTGF is a monoclonal antibody or an active fragment thereof, or is CLN-1 or any derivative thereof. In a further embodiment, a cytotoxic chemotherapeutic agent is also administered to the subject.

Methods for reducing or inhibiting progression of cancer in a subject are also contemplated herein, the method comprising administering to the subject an agent that reduces metastasis of a tumor and that reduces at least one process selected from the group consisting of tumor expansion and tumor cell survival, thereby reducing or inhibiting the progression of cancer in the subject. In certain embodiments, the tumor is a pancreatic tumor.

A method for reducing metastasis of a pancreatic tumor in a subject, the method comprising administering to the subject an agent that inhibits CTGF activity, thereby reducing metastasis, is specifically contemplated herein. The invention further provides methods for reducing pancreatic tumor cell or pancreatic tumor survival in a subject, the method comprising administering to the subject an agent that inhibits CTGF activity, thereby reducing pancreatic tumor cell or pancreatic tumor survival. A method for reducing pancreatic tumor expansion in a subject, the method comprising administering to the subject an agent that inhibits CTGF activity, thereby reducing pancreatic tumor expansion, is also provided.

BRIEF DESCRIPTION OF THE DRAWINGS

FIG. 2 shows growth characteristics of MIA PaCa-2 cells stably transformed with CTGF-encoding expression constructs.

FIG. 3 shows dependence of anchorage independent growth on CTGF.

FIG. 5 shows that cell survival in tumors in situ is correlated with level of CTGF.

FIG. 8 shows cell survival in tumors in situ is dependent upon CTGF.

DETAILED DESCRIPTION OF THE INVENTION

Figure 1:
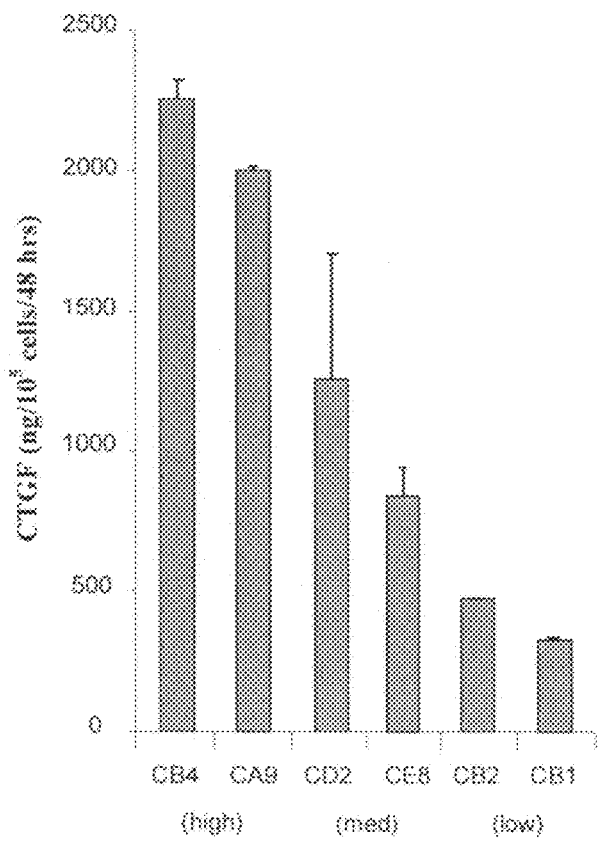
FIG. 1 shows CTGF expression levels in various MIA PaCa-2 clonal cell lines stably transformed with a CTGF-expression construct. Cell lines representing "low" (CB1 and CB2), "medium" (CE8 and CD2), and "high" (CA9 and CB4) CTGF production were used in the examples provided herein.

Before the present compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless context clearly dictates otherwise. Thus, for example, a reference to "a fragment" includes a plurality of such fragments; a reference to an "antibody" is a reference to one or more antibodies and to equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature.

Invention

The present invention provides methods and compounds for treating cancer in a subject, in particular, pancreatic cancer, by inhibiting the expression and/or activity of CTGF. In particular, the invention provides methods for reducing tumor metastasis and for reducing tumor survival and expansion by inhibiting the expression and/or activity of CTGF. In certain embodiments, the invention provides methods for reducing pancreatic tumor metastasis, pancreatic tumor survival, and pancreatic tumor expansion. In another embodiment, the methods reduce or inhibit metastasis of tumors to bone.

In one embodiment, the invention provides a method of reducing or inhibiting tumor expansion in a subject, the method comprising administering to the subject an effective amount of an agent that inhibits CTGF expression and/or activity. Tumor expansion may include various aspects of tumor biology including, but not limited to, modulation of boundary between the tumor and surrounding stroma; signaling and recruitment of neighboring, non-transformed cells; etc. In a particular embodiment, the invention provides a method for inhibiting pancreatic tumor expansion in a subject, the method comprising administering to the subject an effective amount of an agent that inhibits CTGF expression and/or activity. In various embodiments, the subject is a mammal, particularly a human. In various aspects, the agent is an antibody, a small molecule, or an oligonucleotide-based molecule such as aptamers and antisense.

In another embodiment, the invention provides a method of reducing or inhibiting tumor survival in a subject, particularly tumor cell survival, the method comprising administering to the subject an effective amount of an agent that inhibits CTGF expression and/or activity. Tumor cell survival may include various aspects of tumor biology including, but not limited to, modulating apoptotic potential; etc. In a particular embodiment, the invention provides a method for inhibiting pancreatic tumor survival, particularly pancreatic tumor cell survival, in a subject, the method comprising administering to the subject an effective amount of an agent that inhibits CTGF expression and/or activity. In various embodiments, the subject is a mammal, particularly a human. In various aspects, the agent is an antibody, a small molecule, or an oligonucleotide-based molecule such as aptamers and antisense.

In another embodiment, the invention provides a method for reducing or preventing tumor metastasis in a subject, the method comprising administering to the subject an effective amount of an agent that inhibits CTGF expression or activity. Metastasis may involve and include processes at the site of the primary tumor that facilitate tumor invasion of neighboring tissues, organs, etc., or invasion of lymphatic and/or circulatory systems. Metastasis may also involve and include processes at the site of a secondary tumor that facilitates attachment and invasion by the metastasized tumor. Such processes may be due to the cancer cell, e.g., overexpression of CTGF within the cancer cell, etc.; or due to the endogenous tissue at the site of metastasis, e.g., CTGF overexpression by stromal tissue and/or response of bone, liver, etc. to CTGF. In a particular aspect, the invention provides a method for inhibiting or preventing metastasis of a pancreatic tumor in a subject, the method comprising administering to a subject an effective amount of an agent that inhibits CTGF expression or activity. In various embodiments, the subject is a mammal, particularly a human. In various aspects, the agent is an antibody, a small molecule, or an oligonucleotide-based molecule such as aptamers and antisense.

Methods for reducing or preventing mortality associated with cancer, particularly pancreatic cancer, are also provided, the methods comprising administering to a subject having cancer or at risk for having cancer an effective amount of an agent that inhibits the expression and/or activity of CTGF. In various aspects, the subject is a mammal, particularly a human. In various embodiments, the agent is an antibody, a small molecule, or an oligonucleotide-based molecule such as aptamers and antisense.

The present invention establishes for the first time a direct causal relationship between CTGF and the survival and expansion of tumors, particularly pancreatic tumors. Pancreatic tumor, as used herein, includes any tumor located in, derived from, or originating from cells of the pancreas. This includes primary tumors originating in the pancreas, secondary tumors originating in the pancreas or another organ, etc. Further, the present invention demonstrates the explicit correlation between CTGF expression and tumor cell survival, tumor expansion, extent of metastasis, etc. The present invention further demonstrates that agents or compounds that target CTGF, thereby potentially inhibiting the expression and/or activity of CTGF, effectively reduce tumor expansion, increase tumor cell apoptosis, reduce metastasis of tumors, and improve subject survivability. In particular, the invention demonstrates that agents or compounds that target CTGF effectively reduce pancreatic tumor expansion, increase pancreatic tumor cell apoptosis, and reduce metastasis of pancreatic tumors.

Connective Tissue Growth Factor (CTGF)

CTGF is a 36 kD, cysteine-rich, heparin binding, secreted glycoprotein originally isolated from the culture media of human umbilical vein endothelial cells. (Bradham et al. (1991) J Cell Biol 114:1285-1294; Grotendorst and Bradham, U.S. Pat. No. 5,408,040.) CTGF belongs to the CCN (CTGF, Cyr61, Nov) family of proteins, which includes the serum-induced immediate early gene product Cyr61, the putative oncogene Nov, and the Wnt-inducible secreted proteins (WISP)-1, -2, and -3. (See, e.g., O'Brian et al. (1990) Mol Cell Biol 10:3569-3577; Joliot et al. (1992) Mol Cell Biol 12:10-21; Ryseck et al. (1991) Cell Growth and Diff 2:225-233; Simmons et al. (1989) Proc. Natl. Acad. Sci. USA 86:1178-1182; Pennica et al. (1998) Proc Natl Acad Sci USA, 95:14717-14722; and Zhang et al. (1998) Mol Cell Biol 18:6131-6141.) CCN proteins are characterized by conservation of 38 cysteine residues that constitute over 10% of the total amino acid content and give rise to a modular structure with N- and C-terminal domains. The modular structure of CTGF includes conserved motifs for insulin-like growth factor binding proteins (IGF-BP) and von Willebrand's factor (VWC) in the N-terminal domain, and thrombospondin (TSPI) and a cysteine-knot motif in the C-terminal domain.

Although the present invention demonstrates the direct role of CTGF in tumor survival, expansion, and metastasis, and demonstrates that agents targeting CTGF are beneficial in treating cancer, the invention specifically contemplates a similar role for other CCN family members, particularly Cyr61.

CTGF expression is induced by various factors including TGF-β family members, e.g., TGF-⊕1, activin, etc.; thrombin, vascular endothelial growth factor (VEGF), endothelin and angiotensin II. (Franklin (1997) Int J Biochem Cell Biol 29:79-89; Wunderlich (2000) Graefes Arch Clin Exp Opthalmol 238:910-915; Denton and Abraham (2001) Curr Opin Rheumatol 13:505-511; and Riewald (2001) Blood 97:3109-3116; Xu et al. (2004) J Biol Chem 279:23098-23103.) Such factors have been associated with tumorigenesis previously. Therefore, in one aspect the present invention is directed to treatment of cancers whose negative prognosis is correlated with these factors, e.g., TGF-β.

CTGF has been associated with various neoplasms, but its specific role has not been clearly elucidated. CTGF was originally described as a mitogenic factor and was linked to tumor cell proliferation, thereby affecting the formation and growth of the tumor. Expression of CTGF appears to occur in cells both within and bordering the tumor, leading some investigators to suggest that CTGF may facilitate reorganization of the extracellular matrix and promote neovascularization of the tumor. (See, e.g., Shimo et al. (2001) Oncogene 61(4):315-22; Pan et al. (2002) Neurol Res 24(7):677-83; Kondo et al. (2002) Carcinogenesis 23(5):769-76.) CTGF has been implicated in both increased apoptosis, e.g., in breast cancer cells, and increased survival, e.g., in rhabdomyosarcoma cells. (See, e.g., Hishikawa et al. (1999) J Biol Chem 274:37461-37466; Croci et al. (2004) Cancer Res 64:1730-1736.) Therefore, the role of CTGF in cancer may be context-specific, depending on the type and origin of the primary tumor.

CTGF is specifically expressed in malignant lymphoblasts in acute lymphoblastic leukemia (ALL), and CTGF expression is highly correlated with tumor stage in breast cancer and glioma. (See, e.g., Xie et al. (2001) Cancer Res 61:8917-8923; and Xie et al. (2004) Clin Cancer Res 10:2072-2081.) CTGF expression has also been associated with invasive pancreatic cancer, and in breast cancer that metastasizes to bone. (See, e.g., Iacobuzio-Donahue et al. (2002) Am J Pathol 160: 91-99; Kang et al. (2003) Cancer Cell 3:537-549.) In metastatic breast cancer, CTGF is over-expressed in metastatic cells that induce osteolysis, where tumor cell-mediated interaction with and/or degradation of bone matrix releases growth factors that activate osteoclasts leading to bone resorption. Additional metastastic cancers that exhibit prominent osteolytic phenotypes or that metastasize to bone are prostate, hepatocellular carcinoma, colorectal, pancreatic, ovarian, renal cell carcinoma, multiple myeloma, lymphoma, and leukemia.

The present invention, for the first time, demonstrates a direct causal relationship between CTGF and tumor cell survival, tumor expansion, and metastasis of tumors. For example, the present invention demonstrates that tumors derived from MIA PaCa-2 cells transfected with a CTGF expression construct show enhanced tumor cell survival, increased tumor size and invasiveness, and a greater propensity of primary tumors to metastasize; and that animals bearing such tumors show increased mortality. The present invention further demonstrates that tumor expansion, metastasis, and patient mortality correlate with levels of CTGF expression, i.e., mice implanted with cells expressing high levels of CTGF display a higher level of tumor expansion and mortality than mice implanted with cells expressing lower levels of CTGF, e.g., medium-CTGF expressing cells.

Still further, the present invention demonstrates that in vivo administration of an agent that inhibits expression or activity of CTGF slows or prevents tumor expansion. In particular, mice bearing tumors derived from cells expressing medium and high levels of CTGF show reduced tumor expansion and reduced mortality upon treatment with an anti-CTGF antibody. This demonstrates that CTGF expression is causally linked to tumor survival and expansion, and associated host mortality, and that therapeutics targeting CTGF may be effective at retarding tumor expansion and reducing mortality in cancer patients.

Although not to be limited by any particular mechanism, the present invention contemplates the role of CTGF in regulating the activity of NFκB, a transcription factor associated with cell proliferation and cell survival pathways in various disorders including pancreatic cancer. (See, e.g., Algul (2002) Int J Gastrointest Cancer 31:71-78.) Regulation of NFκB likely involves other components of signaling, including, but not limited to, inhibition of IκB and modulation of glycogen synthase kinase (GSK)-3β. (See, e.g., Hoeflich et al. (2000) Nature 406:86-90.) In one aspect, the present invention contemplates a signaling pathway that involves activation of GSK-3β and NFκB by a CTGF-dependent mechanism, and provides agents that modulate the expression and/or activity of CTGF to further modulate downstream GSK-3β and NFκB activity.

Thus, in one aspect, the present methods and compounds are applied to treatment of a wide variety of cancers including, but not limited to, adenocarcinomas, particularly ductal carcinomas as frequently occur in breast and pancreatic cancer; neuroepithelial tumors, e.g., gliomas; gastrointestinal carcinoids, particularly ileal carcinoids; acute lymphoblastic leukemia, rhabdomyosarcoma, and melanoma; and in cancers with a propensity for metastasis to bone, particularly wherein the secondary tumor produces effects on the bone, including osteolytic and osteoblastic lesion formation. In particular aspects, use of the present methods and compounds to treat pancreatic cancer is provided.

Screening Assay

In another aspect, the present invention provides methods for identification of agents or compounds for reducing tumor survival and expansion, particularly tumors of the pancreas. Methods of identifying compounds or agents use various procedures described in the examples herein; e.g., an animal bearing a tumor derived from a CTGF-expressing cell is treated with a compound or agent and tumor expansion and metastasis are measured. An agent that retards or prevents tumor expansion and survival, and/or prevents or reduces tumor metastasis would be selected for use in the present methods.

In one embodiment, the present invention provides a screening assay for identifying an agent that modulates anchorage-independent cell growth (AIG), which is a demonstrated characteristic of tumorigenic cells. The method comprises culturing a CTGF-expressing cell with an agent under conditions suitable, in the absence of the agent, for anchorage-independent growth of the cell; measuring the amount of cell growth that occurs in the presence of the agent; and comparing the amount of cell growth that occurs in the presence of the agent with the amount of cell growth that occurs in the absence of the agent, wherein a change in the amount of cell growth in the presence of the agent relative to the amount of cell growth that occurs in the absence of the agent is indicative of an agent that modulates AIG.

In certain embodiments, the cells used in the assay express CTGF endogenously, whereas in other embodiments the cells have been recombinantly modified to express CTGF. Any cell expressing CTGF can be utilized in the assay. In some embodiments described herein, the cell is a PANC-1 cell. PANC-1 cells are ductal epithelioid carcinoma cells originally obtained from a primary pancreatic cancer. (Lieber et al. (1975) Int J Cancer 15:741-747.) In other embodiments described herein, the cell is a MIA PaCa-2 cell recombinantly modified to express CTGF. MIA PaCa-2 cells were originally obtained from a human primary pancreatic cancer. (Yunis et al. (1975) Int J Cancer 19:128-135.) When the cells have been modified to express CTGF, the CTGF can be any naturally occurring CTGF protein, e.g., human CTGF, mouse FISP-12, etc; or any synthetic CTGF protein retaining the requisite activity, i.e., modulation of AIG, of a naturally-occurring CTGF. In a particular embodiment, the CTGF is human CTGF. The cells typically express sufficient amounts of CTGF to produce measurable activity, e.g., cell survival, colony expansion, etc., in a given period of time. For example, when approximately $10^5$ cells producing endogenous CTGF or stably transfected with a CTGF expression construct are placed in an appropriate growth medium and cultured for 48 hours, at least 0.3 μg CTGF, and more specifically about 0.3 to 2.2 μg CTGF, will be produced and secreted into the medium.

In particular embodiments of the screening assay, cells expressing CTGF may be dispersed in a semi-solid support medium appropriate for AIG. In one embodiment, the semi-solid support medium comprises agar, e.g., Noble Agar. The agar can be at any suitable concentration to support AIG; in one particular embodiment, the agar is at a concentration of about 0.35%. Cell growth can be measured by any method known to those of skill in the art. In one embodiment, cell growth comprises counting clusters of cells in a defined area of the semi-solid support medium. In another embodiment, cell growth comprises measuring average cluster size.

Compounds and Agents

Various compounds and agents can be used in the present methods. The compounds and agents modulate CTGF activity, such activity including, but not limited to, expression of CTGF by a cell and alterations in cell phenotype due to CTGF. Alterations in cell phenotype may include modification of cell surface or intracellular macromolecules, such as proteins, e.g., by phosphorylation or de-phosphorylation; changes in gene expression as detected, e.g., by microarray or quantitative PCR analysis; and/or changes in protein expression and/or secretion, e.g., increased production of collagen by a cell. Alterations in cell phenotype may also include, but are not limited to, gross changes in cell shape, adhesion of a cell to another cell and/or to extracellular matrix, and cell motility as measured, e.g., in a Boyden chamber assay. In particular, compounds and agents for use in the present methods modulate anchorage-independent growth of a cell as measured, e.g., in an assay as described above or provided in the examples herein.

In some embodiments, the agent is an antibody that specifically binds to CTGF. In a preferred embodiment, the antibody is a monoclonal antibody. In another preferred embodiment, the antibody is a human or humanized antibody. Antibodies that bind to CTGF are described in U.S. Pat. No.5,408,040; International Publication No. WO 99/07407; International Publication No. WO 99/33878; and International Publication No. WO 00/35936, each of which reference is incorporated herein in its entirety. In particular embodiments, the agent comprises CLN-1, described in International Publication No. WO 2004/108764, which reference is incorporated herein in its entirety. Any antibody that specifically binds to CTGF, such as any of the above-described antibodies, may be used in the present methods in its entirety, or may be modified to obtain a portion of the antibody that retains appropriate activity against CTGF, e.g., epitope-binding activity, and which portion can thus be used in the present methods. For example, an antibody derived from CLN-1 may comprise a CLN-1 light chain, a CLN-1 heavy chain, or variable domains of the heavy and light chain. In one particular embodiment, the antibody of CLN-1 is the antibody produced by the chinese hamster ovary (CHO) cell line deposited with the American Type Culture Collection (ATCC; 10801 University Boulevard, Manassus, VA 20110-2209) on 20 May 2004 and having the ATTC accession no. PTA-6006. Antibodies, or fragments thereof, can be administered by various means known to those skilled in the art. For example, antibodies are often injected intravenously, intraperitoneally, or subcutaneously. Antibody formulations may also be injected intraarticularly, intraocularly, intradermally, intrathecally etc.

In other embodiments, the agent is a small molecule. Small molecule inhibitors of CTGF expression and/or activity have been described; for example, International Publication No. WO 96/38172 identifies modulators of cAMP such as cholera toxin and 8Br-cAMP as inhibitors of CTGF expression. Therefore, compounds known to increase cAMP level in cells, e.g., prostaglandin and/or prostacyclin analogs such as Iloprost; phosphodiesterase IV inhibitors; etc., may be used to modulate CTGF expression. (See, e.g., International Publication No. WO 00/02450; Ricupero et al. (1999) Am J Physiol 277:L1165-1171; also, see Ertl et al. (1992) Am Rev Respir Dis 145:A19; and Kohyama et al. (2002) Am J Respir Cell Mol Biol 26:694-701.) Also, inhibitors of serine/threonine mitogen activated kinases, particularly p38, cyclin-dependent kinase, e.g. CDK2, and glycogen synthase kinase (GSK)-3 have also been implicated in decreased CTGF expression and/or signaling. (See, e.g., Matsuoka et al. (2002) Am J Physiol Lung Cell Mol Physiol 283:L103-L112; Yosimichi et al. (2001) Eur J Biochem 268:6058-6065; International Publication No. WO 01/38532; and International Publication No. WO 03/092584.) Such agents can be used to reduce expression/activity of CTGF and thereby ameliorate or prevent the pathological processes induced by CTGF. Such compounds can be formulated and administered according to established procedures within the art. (See, e.g., Gennaro, Ed. (2000) Remington's Pharmaceutical Sciences, 20$^{th}$ edition, Mack Publishing Co., Easton Pa.; and Hardman, Limbird, and Gilman, Eds. (2001) The Pharmacological Basis of Therapeutics, 10$^{th}$ Edition, McGraw Hill Co, New York N.Y.)

In various embodiments, the agent is an antisense or aptamer oligo- or polynucleotide. Antisense technologies, including small interfering ribonucleic acids (siRNAs), micro-RNAs (miRNAs), ribozymes, and antisense sequences directed to modulate CTGF expression may also be used to inhibit tumor expansion and survival, and metastasis, and to decrease associated mortality rates. (See, e.g., Zeng (2003) Proc Natl Acad Sci USA 100:9779-9784; and Kurreck (2003) Eur J Biochem 270:1628-1644.) Antisense constructs that target CTGF expression have been described and utilized to reduce CTGF expression in various cell types. (See, e.g., International Publication No. WO 96/38172; International Publication No. WO 00/27868; International Publication No. WO 00/35936; International Publication No. WO 03/053340; Kothapalli et al. (1997) Cell Growth Differ 8(1):61-68; Shimo et al. (1998) J Biochem (Tokyo) 124(1): 130-140; and Uchio et al. (2004) Wound Repair Regen 12:60-66.) Such antisense constructs can be used to reduce expression of CTGF and thereby ameliorate or prevent CTGF-modulated effects, e.g., tumor progression and/or metastasis, etc. Such constructs can be designed using appropriate vectors and expressional regulators for cell- or tissue-specific expression and constitutive or inducible expression. These genetic constructs can be formulated and administered according to established procedures within the art.

Aptamers that modulate CTGF activity may be RNA or DNA oligonucleotides or proteins identified, e.g., using the screening assay provided herein. Aptamers are generally identified through a process called SELEX (systematic evolution of ligands by exponential enrichment), an iterative screening process for selection and amplification of an aptamer having appropriate activity and selectivity. (See, e.g., Ellington and Szostak (1990) Nature 346:818-822; Klug and Famulok (1994) Mol Biol Rep 20:97-107; and Brody and Gold (2000) J Biotechnol 74:5-13.) Aptamer libraries, typically composed of, e.g., single stranded DNA or RNA oligonucleotides containing a central region of randomized sequences flanked by constant regions for subsequent transcription, reverse transcription, and DNA amplification, are readily available or prepared. (See, e.g., Fiegon et al. (1996) Chem Biol 3:611-617.)

In some aspects, compound or agent is administered to a subject to reduce or prevent tumor cell survivability, tumor expansion, and tumor metastasis. In certain embodiments, the compound or agent specifically and selectively targets CTGF, e.g., inhibiting the expression and/or activity of CTGF with no significant effect on other factors. In other embodiments, the compound or agent specifically and selectively targets CCN family members, e.g., inhibiting the expression and/or activity of CCN family members with no significant effect on other factors. In particular aspects, the CCN family members are selected from the group consisting of CTGF and Cyr61.

The compound or agent may be administered alone or in combination with one or more additional therapeutic agents. For example, a compound or agent that targets CTGF may sensitize the tumor to the action of a second therapeutic agent and be used to limit or reduce tumor cell survivability, i.e., provide a cytostatic effect; or may reduce tumor mass, i.e., provide a selective cytoxic effect; while a traditional chemotherapeutic or radiation may be used to reduce tumor mass, i.e., provide a non-specific cytotoxic effect. Use of the present methods in this context would allow the use of smaller doses of chemotherapeutic or radiation to achieve the desired end result, thus reducing adverse side effects commonly associated with traditional non-specific cancer therapies. Additionally, the compound or agent may be combined with a second therapeutic agent, e.g., an anti-angiogenic agent such as Avastin; an anti-receptor tyrosine and/or serine/threonine kinase agent such as Tarceva, etc.

These and other embodiments of the present invention will readily occur to those of ordinary skill in the art in view of the disclosure herein.

EXAMPLES

The invention will be further understood by reference to the following examples, which are intended to be purely exemplary of the invention. These examples are provided solely to illustrate the claimed invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications are intended to fall within the scope of the appended claims.

Example 1

Generation of Cell Lines Expressing Different Levels of CTGF

MIA PaCa-2 cells (American Type Culture Collection (ATCC), Manassas Va.) are reportedly insensitive to the growth inhibitory effects of TGF-β1. (See, e.g., Freeman et al. (1995) J Cell Physiol 165:155-163.) To determine if MIA PaCa-2 cells would provide a suitable host for exogenous CTGF expression, both constitutive and TGFβ-inducible expression of CTGF was determined by measuring CTGF levels in cell culture supernatants using an ELISA assay that measures both cleaved N-terminal fragment and whole CTGF. (See International Publication No. WO 03/024308, incorporated by reference herein in its entirety.) As CTGF expression was not detected in either untreated or TGF-β2-treated cultures, MIA PaCa-2 cells were used to generate cells expressing various levels of CTGF.

MIA PaCa-2 cells were transfected with pSCMV-Puro-CTGF, an adenoviral construct encoding full-length CTGF and the puromycin antibiotic-resistance gene, using lipofectamine 2000 reagent (Invitrogen Life Technologies, Carlsbad Calif.) according to procedures supplied by the manufacturer. Individual clones were selected based on their resistance to puromycin, and CTGF expression and protein levels were determined by quantitative RT-PCR and ELISA assay, respectively. A series of clones were isolated and characterized, and representative clones that exhibited low (clones CB1 and CB2), medium (clones CE8 and CD2), and high (clones CA9 and CB4) levels of CTGF expression and protein production were identified. On plating $10^5$ cells, the low-, medium-, and high-CTGF expressing clones showed clear differences in CTGF expression as determined by quantitative RT-PCR, with secreted levels of CTGF ranging from a low of about 0.3 to a high of about 2.2 µg CTGF/48 hrs. (FIG. 1.)

MIA PaCa-2 cells transfected with vector encoding the puromycin resistance gene, but not with CTGF, served as control (vector). As was seen in the MIA PaCa-2 parental cell line, cells transfected with control vector did not express detectable levels of CTGF transcript or protein.

Example 2

CTGF Enhances Anchorage-independent Growth

Figure 2A:
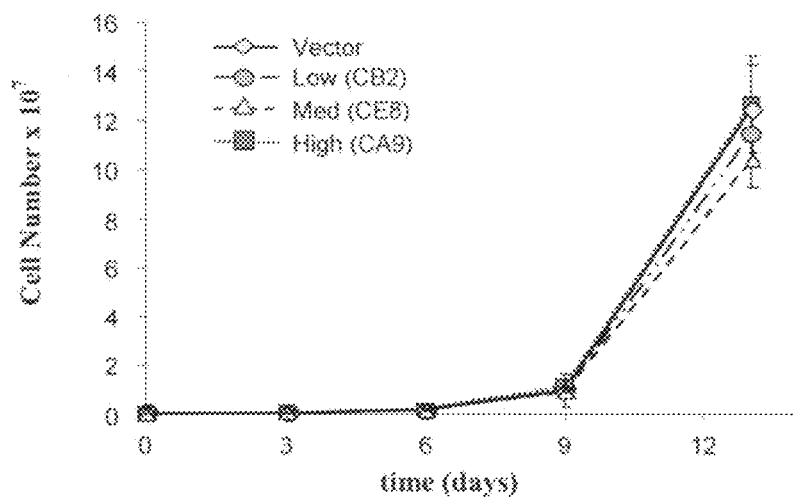
FIG. 2A shows that the level of CTGF produced by MIA PaCa-2 cells does not affect cell growth when cultured on a 2-dimensional surface.

In vitro cellular growth rates of vector control and low-, medium-, and high-CTGF expressing clones were measured to determine whether higher levels of CTGF expression alter the ability of tumor cells to survive and/or proliferate. Clonal cell lines were cultured in standard culture plates for up to 12 days, with cells harvested and counted after 3, 6, 9 and 12 days. No difference in the rate or level of cell accumulation was seen between vector control cells and cells expressing different levels of CTGF (FIG. 2A).

AIG is a common characteristic of cancer cells. Although CTGF apparently was unable to induce AIG independently, it was required for the induction of AIG by TGF-β1. (See, e.g., Frazier et al. (1996) J Invest Dermatol 107:404-411; and Kothapalli et al. (1997) Cell Growth Differ 8:61-68.) MIA PaCa-2 cells reportedly have a colony-forming efficiency in soft agar of approximately 19%. (Yunis et al. (1977) Int J Cancer 19:128-135.) To determine the effect of CTGF expression on AIG in MIA PaCa-2 cells, clones expressing various levels of CTGF (CA9, CB1, CB4, and CD2) or containing vector alone (VA2, VA6, VB1, and VB4) were analyzed for their ability to grow in soft agar.

In duplicate experiments, approximately $1.2 \times 10^3$ cells from each clone were distributed in 2.0 ml of 0.35% Noble Agar containing 10% fetal bovine serum (FBS) and 10% newborn calf serum (NCS). Each embedded cell mixture was overlaid on 1.5 ml of 0.7% Noble Agar in 6-well plates, and a 1.5 ml top layer of 0.7% Noble Agar was added to each well to prevent evaporation. Plates were incubated for 11 days in a humidified incubator at 37° C., 5.0% $CO_2$. The number of colonies was enumerated by counting a 1.5 cm-by-1.5 cm grid under a microscope. Total colony counts were extrapolated to the entire plate based on the ratio of the surface area of each well to the surface area of the grid. Colony morphologies were photographed at 20× magnification.

Figure 2B:
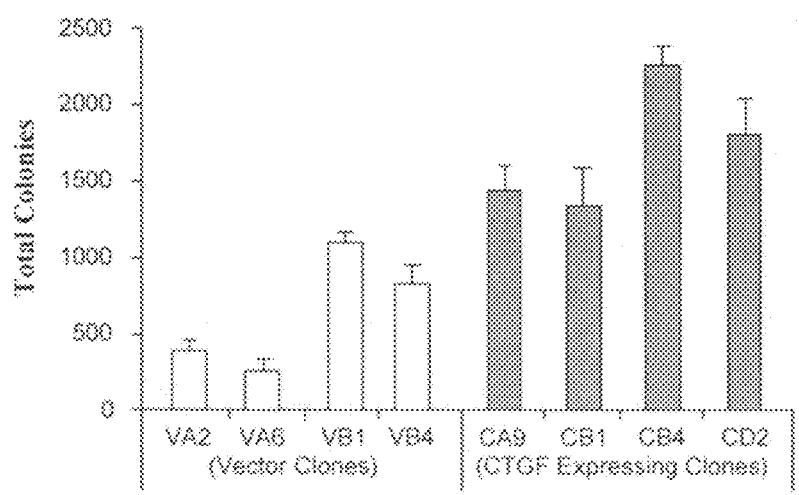
FIG. 2B, however, shows that the level of CTGF produced does affect cell growth and colony formation when cells are cultured in a soft agar medium.
Figure 3A:
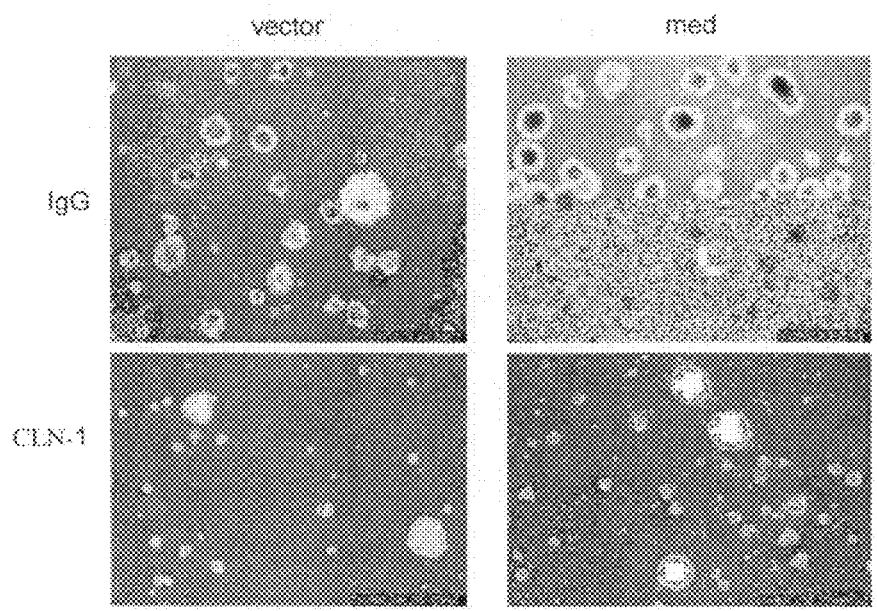
FIG. 3A shows images of cells expressing no (vector) or medium levels (med) of CTGF. Top panels show that CTGF increases the number and appearance of soft agar colonies; lower panels show that treatment with an antibody that binds CTGF substantially reduces both number and size of colonies.

Although MIA PaCa-2 cells transformed with vector alone demonstrated AIG, the number of colonies formed increased with increasing CTGF expression. (FIG. 2B.) The top panels in FIG. 3A show colony morphology of CTGF-expressing clones and null vector clones, respectively. More colonies formed in CTGF-expressing clones, and colonies arising from CTGF-expressing clones were generally larger than colonies arising from null vector clones. These results demonstrate that CTGF enhances anchorage-independent growth of MIA PaCa-2 cells, and higher levels of CTGF expression result in larger colony size.

Example 3

Agents Inhibiting CTGF Reduce Anchorage-independent Growth

As CTGF enhances AIG (see above example), agents that reduce CTGF activity and/or availability were tested in the AIG assay to determine if they could reduce colony formation. The ability of antibodies that specifically target CTGF, such as those generally described in U.S. Pat. No. 5,408,040, to inhibit AIG in MIA PaCa-2 cells was tested using the soft agar assay as described above with the following modifications. A human monoclonal antibody, CLN-1 (see International Publication WO 2004/108764), which specifically binds CTGF, or a control human IgG was added at a final concentration of 100 µg/ml to soft agar containing CTGF-expressing clone CD2 cells or null vector clone VA6 cells. Plates were re-fed on day 5 with 1.5 ml top layer containing 100/g/ml of CLN-1 or human IgG. Plates were incubated for 11 days and assessments were carried out as described above.

Figure 3B:
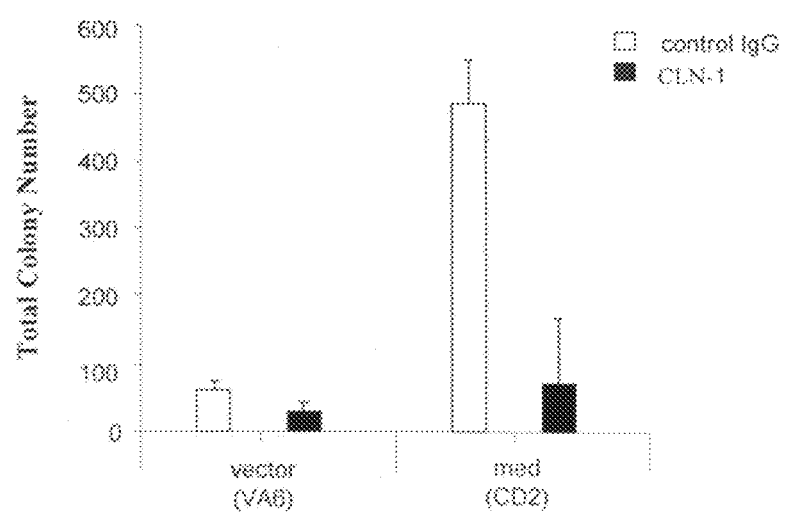
FIG. 3B shows a quantitative difference in colony number due to CTGF expression level and antibody treatment.

As shown visually in the lower panels of FIG. 3A, CLN-1 treatment significantly inhibited colony formation by the CTGF-expressing cells. Quantification of the result shows that antibody reduced colony formation by CTGF-expressing cells approximately 85%, but produced only a weak inhibition in colony formation by the vector clones. (FIG. 3B.) Control IgG had no effect on basal colony formation by either vector control or CTGF-expressing cells. The results demonstrate that therapeutics targeting CTGF activity and/or availability are effective in reducing or inhibiting anchorage independent growth in MIA PaCa-2 pancreatic cancer cells and potentially in cancer cells generally.

Example 4

CTGF Enhances Tumor Expansion and Increases Host Mortality

Female 8 to 10 week old SCID (severe combined immune deficient; Simonsen Laboratories, Inc., Gilroy Calif.) or athymic nude (nu/nu; Harlan, Indianapolis Ind.) mice were injected subcutaneously with approximately $10^7$ cells from control, low-, medium-, or high-CTGF expressing MIA PaCa-2 clones. Injected mice were monitored for tumor expansion, with tumor size and volume (calculated as length× width×height) measured at weekly intervals. Measurements for animals receiving injection of the same clone type were averaged. Tumors were excised and embedded in paraffin. Sequential 4 µm paraffin sections were stained with rabbit antibody (1:50; Zymed Laboratories, Inc., South San Francisco Calif.) directed against the Ki-67 nuclear antigen, which is only present in proliferating cells (Gerdes et al. (1984) J Immunol 133:1710-1715), to quantify proliferative cells. Detection was performed using biotinylated secondary antibodies in combination with horseradish-peroxidase-coupled streptavidin (Jackson ImmunoResearch Laboratories, Inc., West Grove Pa.) and diaminobenzidine substrate (Invitrogen). Separate sections were stained by terminal deoxynucleotidyl transferase biotin-dUTP nick end labeling (TUNEL), which identifies apoptotic cells, using the DEAD-END fluorometric TUNEL system (Promega, Madison Wis.) according to the manufacturer's instructions. Briefly, sections were deparaffinized and rehydrated, permeabilized in proteinase K, and treated with terminal deoxynucleotidyl transferase incubation buffer at 37° C. for 60 minutes in the dark. Sections were counterstained with 4'-6-Diamidino-2-phenylindole (DAPI, Sigma).

The percentage of proliferating (Ki-67-positive) and apoptotic (TUNEL positive) tumor cells was determined in four randomly selected areas of tumor sections using a Nikon Eclipse E800 microscope at 400× magnification. At least 400 cells per high power field were counted to determine the percentage of positive cells. Mean values and standard deviations were calculated.

Figure 4A:
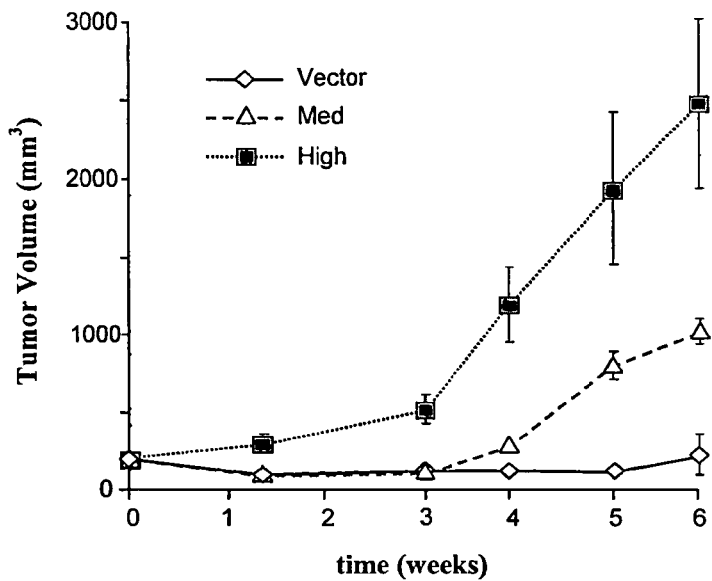
FIGS. 4A and 4B show changes in tumor volume and mortality, respectively, in mice bearing tumors derived from the medium- and high-CTGF expressing cells.
Figure 4B:
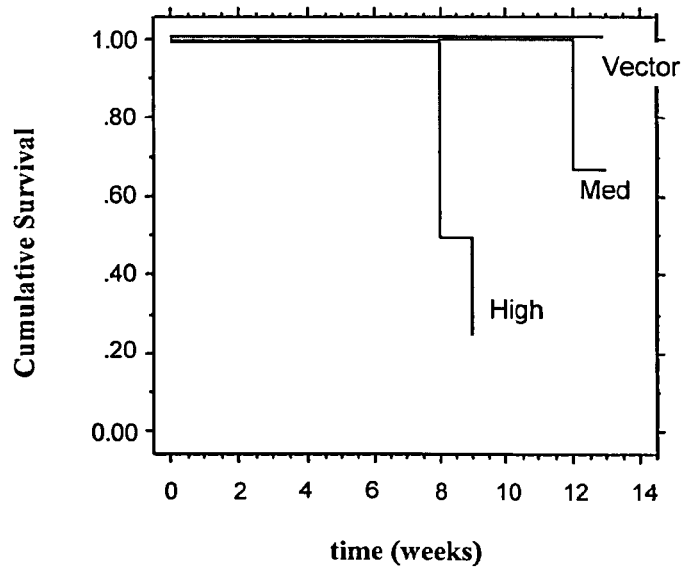
Figure 5A:
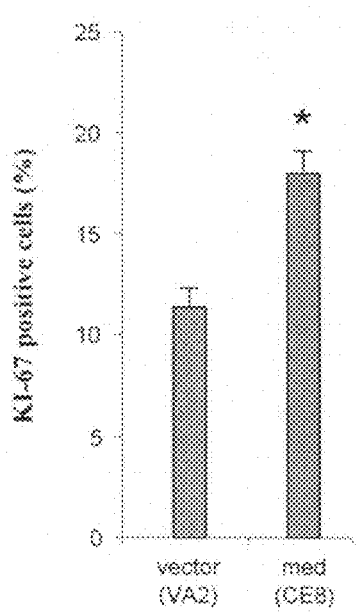
FIG. 5A shows an increase in proliferating cells and FIG. 5B shows a decrease in apoptotic cells in tumors derived from CTGF expressing cells relative to vector control cells.
Figure 5B:
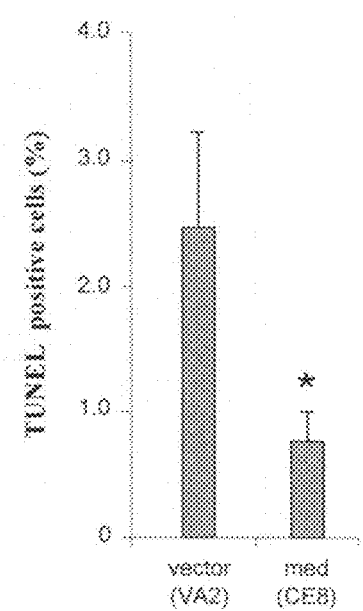

Mice injected with CTGF-expressing clones exhibited enhanced tumorigenesis proportional to the level of CTGF expression, as exemplified by increase in tumor volume over time in animals injected with control, medium, and high expressing cells. (FIG. 4A.) Mice implanted with control MIA PaCa-2 cells showed essentially no tumor expansion. (FIG. 4A.) Furthermore, increased expression of CTGF in cell implants correlated with increased mortality in injected animals; FIG. 4B shows a Kaplan-Meier Cumulative Survival Plot through time to last follow up or time of death. CTGF-expressing tumors also showed increased numbers of actively proliferating cells (FIG. 5A) and reduced numbers of actively apoptotic cells (FIG. 5B) within the tumor. Although CTGF was originally described as a mitogenic factor (see, e.g., Bradham et al. (1991) J Cell Biol 114:1285-1294), the increased cell proliferation may be directly or indirectly induced by CTGF. These results demonstrate that CTGF is directly involved in tumor expansion, and is thereby a target for therapeutic agents that may reduce or inhibit tumor expansion in vivo. In particular, agents that block or neutralize CTGF function may provide therapeutic benefit in tumor-bearing patients.

Example 5

Plasma and Urine Levels of CTGF

As CTGF is a secreted factor, increased production of CTGF by an expanding tumor mass would lead to increased CTGF in the surrounding stroma and, potentially, throughout the circulation of the host. To determine whether tumor-bearing hosts had higher circulating levels of CTGF, urine and plasma samples were collected from mice following injection of MIA PaCa-2 clones and expansion of detectable tumor mass. Plasma samples were also obtained by terminal bleed. CTGF levels were measured using the ELISA assay described in Example 1. (See International Publication No. WO 03/024308.) CTGF expression levels were also reassessed in culture supernatants from control clones or those expressing low, medium or high levels of CTGF.

Figure 6C:
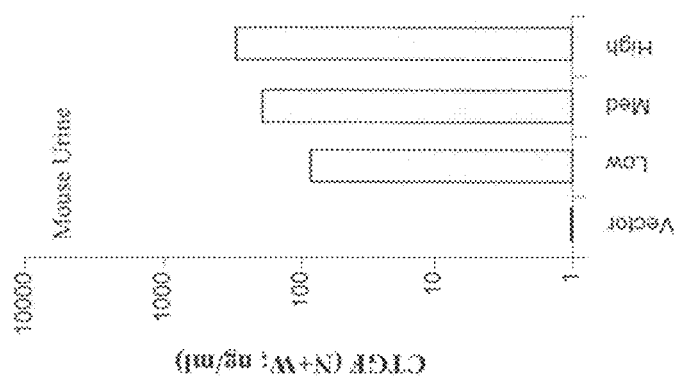
FIGS. 6A, 6B, and 6C show correspondence between CTGF expression level in vitro and plasma and urine CTGF levels in tumor-bearing animals for low-, medium-, and high-CTGF expressing cells and tumors derived therefrom.
Figure 6B:
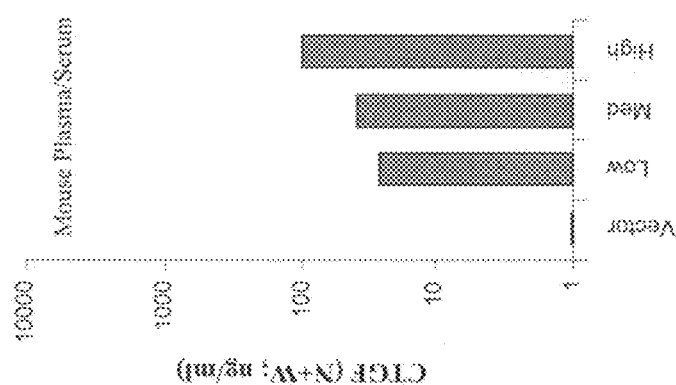
Figure 6A:
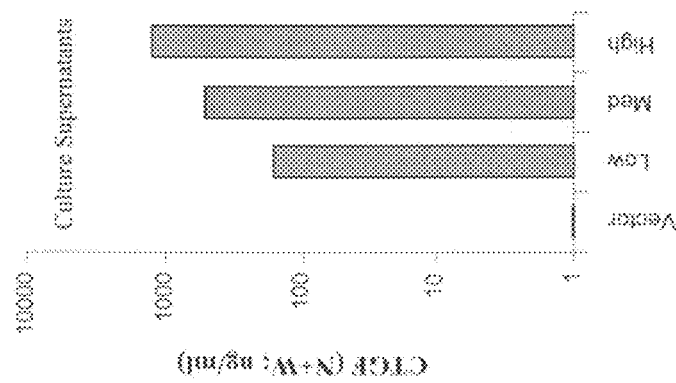

The level of CTGF present in both plasma (FIG. 6B) and urine (FIG. 6C) of tumor-bearing hosts mimicked CTGF expression observed in vitro in culture supernatants of the respective MIA PaCa-2 clones (FIG. 6A). Thus, mice implanted with high CTGF expressing clones exhibited the highest levels of circulating and excreted CTGF, and animals implanted with low CTGF expressing cells exhibited the lowest detectable levels of circulating and excreted CTGF. The levels of circulating and urinary CTGF levels in animals injected with control cells were undetectable. The data demonstrate a direct correlation between CTGF expression levels in the tumor and CTGF levels found in body fluids, suggesting tumors secrete CTGF directly into their environment.

Since the degree of CTGF expression in tumor cells may directly correlate with increased tumor expansion and survival, and the level of CTGF produced by a tumor is proportional to the level of CTGF in body fluids such as blood and urine, measurement of CTGF in, e.g., plasma or urine of cancer patients may be indicative of tumor stage or correlate with tumor burden, which would be a valuable diagnostic and prognostic biomarker for disease assessment.

Example 6

Agents Inhibiting CTGF Reduce Tumor Expansion 6.1 Subcutaneous Implantation of CTGF-expressing MIA PaCa-2

In two separate studies, mice were implanted subcutaneously with either medium or high CTGF expressing MIA PaCa-2 clones and tumor size and volume were determined in each set of animals at weekly intervals. When tumors reached a volume of approximately 250 mm$^3$, animals were stratified to receive either 20 mg CLN-1 per kg body weight or phosphate buffered saline (antibody vehicle) twice a week. Measurement of tumor size and volume was continued for each group of animals at weekly intervals.

Figure 7A:
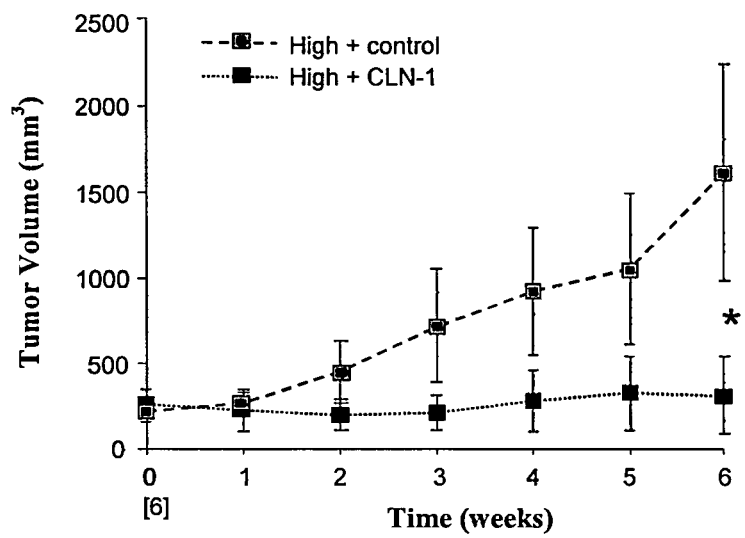
FIGS. 7A and 7B show that therapeutics targeting CTGF effectively reduce survival and expansion of tumors derived from MIA PaCa-2 cells expressing high levels of CTGF and Panc-1 cells, respectively.

Administration of antibody to nude mice implanted with high CTGF expressing clones resulted in slowed tumor expansion, particularly apparent after approximately two weeks of therapy. (FIG. 7A.) Similarly, administration of antibody to animals implanted with medium CTGF expressing clones resulted in reduced tumor expansion as compared to animals receiving vehicle control. The data show that administration of an agent targeting CTGF, e.g., a CTGF-specific monoclonal antibody, leads to reduction in tumor expansion shortly after initiation of therapeutic administration, e.g., after one to two weeks of treatment.

Therapeutic agents targeting CTGF exert benefits at various stages of tumor progression. For example, high-CTGF expressing cells were subcutaneously injected into mice to generate xenograft tumors as described above. In one cohort, mice were administered 20 mg/kg CLN-1 twice a week beginning approximately two days after injection of cells. In a second cohort, tumors were allowed to expand to a volume of approximately 250 mm$^3$, at which time the cohort was stratified and either left untreated or treated with 20 mg/kg antibody twice a week. Measurement of tumor size and volume was continued for each group of animals at weekly intervals. In both cohorts, administration of antibody reduced tumor expansion.

In a similar study, high CTGF expressing cells were subcutaneously injected into mice to generate xenograft tumors as described above, with one cohort of mice left untreated and one cohort administered 20 mg/kg antibody therapy twice a week beginning approximately two days after tumor implantation. Consistent with results shown above, administration of antibody inhibited tumor expansion and progression, such that by 8 weeks after implantation the vehicle control treated mice had average tumor volumes approximately twice that of the antibody-treated cohort. However, termination of antibody therapy at 8 weeks resulted in resumption of tumor expansion.

The data show that administration of therapeutic agents targeting CTGF reduces or prevents tumor expansion at various stages of tumor progression. Thus, agents that block CTGF may provide therapeutic benefit in cancer patients that present with either early stage or clinically established tumors. The results demonstrate that agents targeting CTGF may provide benefit to cancer patients at various stages of disease, retarding expansion of early and late stage tumors.

Such therapy may be particularly advantageous in combination with a second therapeutic method that exerts a cytotoxic effect, e.g., traditional chemotherapy or radiation therapy. The CTGF-directed therapeutic would effectively prevent tumor expansion, while the cytotoxic therapy destroyed the existing tumor mass.

6.2 Subcutaneous Implantation of PANC-1

Figure 7B:
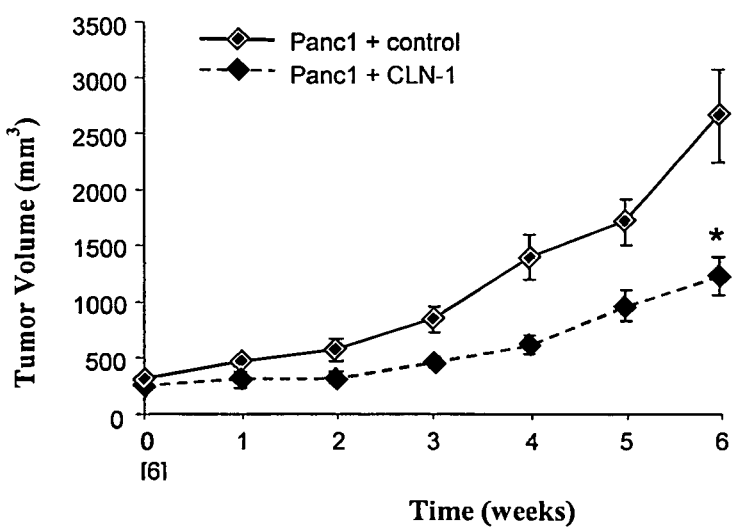

Nude mice (Harlan) were implanted subcutaneously with PANC-1 cells in a procedure analogous to the one described in Example 6.1. Mice injected with PANC-1, which express CTGF endogenously, exhibited an increase in tumor volume over time. (FIG. 7B.) As was seen with tumors derived from CTGF-expressing MIA PaCa-2 cells, administration of antibody CLN-1 to animals implanted with PANC-1 resulted in slowed tumor expansion. (FIG. 7B.) Again the data show that administration of therapeutic agents targeting CTGF reduce or prevent tumor expansion.

Figure 8A:
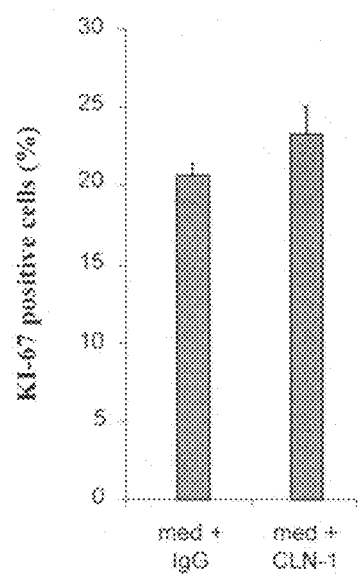
FIG. 8A shows a therapeutic targeting CTGF does not significantly alter the proliferative capacity of the cells.
Figure 8B:
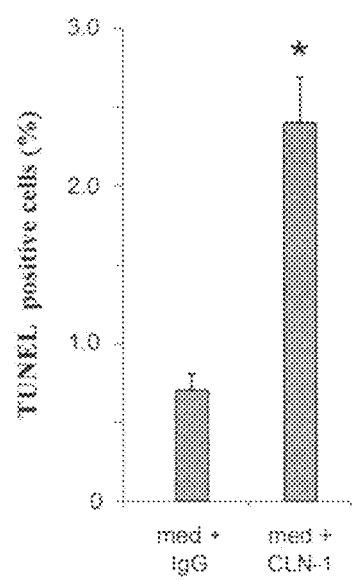
FIG. 8B shows that an agent targeting CTGF significantly increases apoptosis.

Analysis of tumors for proliferating and apoptotic cells, using methods described above, showed that agents targeting CTGF do not significantly affect the number of proliferating cells in the tumor (FIG. 8A), but do restore apoptotic activity of cells within the tumor (FIG. 8B). These results suggest that CTGF is important for survival of proliferating cells, thus increasing cell mass by maintaining the viability of proliferating cells and reducing cell apoptosis. The results further demonstrate that administration of an agent that targets CTGF provides therapeutic benefit.

6.3 Orthotopic Implantation of PANC-1

Tumors were initiated by subcutaneous injection of approximately 10$^6$ PANC-1 cells into the flank of nude mice (Harlan). After 2-6 weeks the cells formed primary tumors that were aseptically resected, immediately minced into 2-mm$^3$ pieces, and implanted into the pancreas of naïve nude mice via a surgical flap. Mice were randomized to receive either phosphate buffered saline (vehicle control; n=4) or 20 mg/kg CLN-1 administered by intraperitoneal injection, with dosing initiated 2 weeks after tumor fragment implantation and dosed twice weekly thereafter. Treatment was continued for a total of 6 weeks, at which time control mice had developed large abdominal tumor masses, and all the mice were sacrificed. Primary tumor volumes were calculated using the equation: VOLUME=(L×H×W)×π/4, where L, H, and W are the length, height, and width of the tumor.

Figure 9:
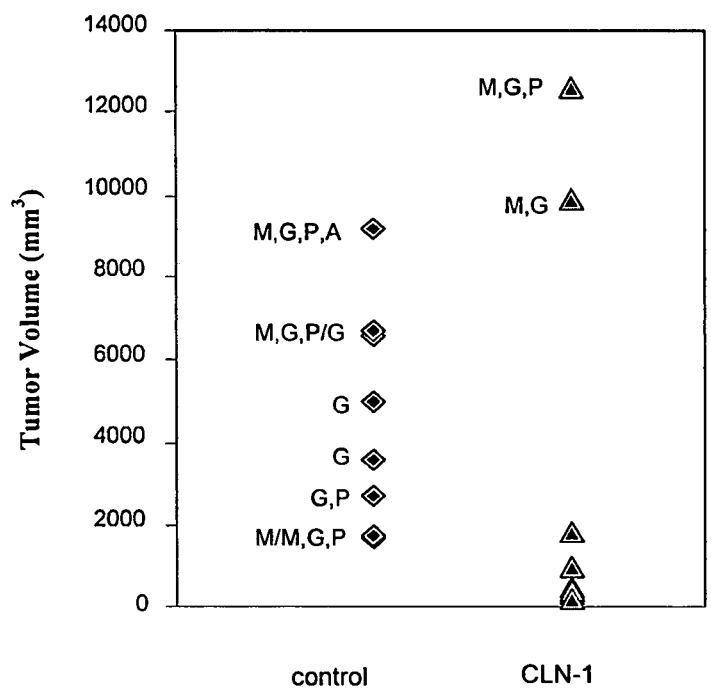
FIG. 9 shows survival, expansion, and metastasis of tumors derived from orthotopic implantation of PANC-1 cells into the pancreas of mice, and the ability of an agent targeting CTGF to reduce both survival and metastases of the tumors.

Compared to tumor-bearing animals receiving only vehicle control, animals administered CTGF-specific antibody produced tumors approximately 83% smaller, presumably due to reduced rate of tumor cell survivability. (FIG. 9.) The result shows that antibodies specific for CTGF reduce the expansion of orthotopic pancreatic tumors in vivo. Additional data using an anti-CTGF antibody that binds host-derived mouse CTGF, but not PANC-1-derived human CTGF, suggest CTGF derived from both the tumor and surrounding normal tissue may be involved in tumor expansion. Thus, similar to results presented above, the present experiment demonstrates that agents targeting CTGF may provide therapeutic benefit in treating patients with pancreatic cancer by reducing or preventing tumor expansion and/or progression.

Example 7

Agents Inhibiting CTGF Reduce Tumor Metastasis

Experimental animals that were treated as described in Examples 6.2 were assessed visually at autopsy for any evidence of tumor metastases to axillary and inguinal lymph nodes. Table 1 shows lymph node metastases in animals treated with CLN-1 relative to animals treated with vehicle control. As shown in the table, 5 out of 6 tumors metastasized to lymph nodes in control animals, whereas only 1 out of 5 tumors metastasized in antibody-treated animals.

TABLE 1

| Control antibody | | | CLN-1 | | |
|---|---|---|---|---|---|
| | Macroscopic LN metastasis | | | Macroscopic LN metastasis | |
| Tumor # | Axillary | Inguinal | Tumor # | Axillary | Inguinal |
| 1 | − | + | 1 | + | + |
| 2 | + | + | 2 | − | − |
| 3 | + | + | 3 | − | − |
| 4 | + | − | 4 | − | − |
| 5 | + | + | 5 | − | − |
| 6 | − | − | | | |

Experimental animals that were treated as described in Examples 6.3 were assessed visually at autopsy for any evidence of tumor metastases to proximal and distal lymph node and other sites within the peritoneum. Primary tumor volume and sites of metastases were further analyzed and details for each animal are provided in FIG. 9. In the figure, symbols represent tumor volume, and letters beside the symbol indicate sites of metastasis as follows: M=mesenteric, G=gastric, P=peritoneal, and A=ascites.

The results demonstrate that therapeutics targeting CTGF not only reduce tumor expansion and survivability, but significantly reduce metastasis of the primary tumor to secondary sites. Therefore, agents targeting CTGF may provide therapeutic benefit in treating patients with cancer, particularly pancreatic cancer, by reducing tumor expansion and reducing or preventing metastasis of existing tumors.

Example 8

Agents Inhibiting CTGF Affect Tumor Microvessel Formation

Tumors derived from the experimental animals described in Example 6.3 (supra) were embedded and frozen in OCT compound prior to being sectioned and stained with a rat anti-mouse CD31 monoclonal antibody and counterstained with hematoxylin. A total of three angiogenic hot-spots per slide were analyzed and scored for blood vessel number, and quantitated for microvessel density using an Image Pro Plus version 4.5.1 image analysis program (Media Cybernetics, Silver Spring, Md.). Microvessel density was calculated as the ratio of positively stained areas to the total area of the image or field.

As compared to tumor-bearing animals that received vehicle control, the number and density of tumor blood vessels was reduced by 45% and 61%, respectively, in animals receiving CLN-1. The results indicate that agents targeting CTGF reduce the number and density of blood vessels that form in primary tumors, particularly pancreatic tumors. A reduction in vascularization may be one mechanism by which CTGF limits tumor expansion, and provides further support for the use of agents targeting CTGF for treatment of various cancers, particularly highly vascularized cancers.

The present invention demonstrates that therapeutic agents targeting CTGF are effective at preventing or reducing tumor expansion, and decreasing the number and density of microvessels within tumors. The invention further demonstrates that therapeutic agents targeting CTGF are additionally effective at reducing and/or preventing metastasis of the primary tumor to the lymphatic system and/or other organs. Together, the data indicate that agents targeting CTGF may provide therapeutic benefit in pancreatic and other neoplastic disease by inhibiting the capacity of tumors to expand, survive, and metastasize to other sites within the body.

Various modifications of the invention, in addition to those shown and described herein, will become apparent to those skilled in the art from the foregoing description. Such modifications are intended to fall within the scope of the appended claims.

All references cited herein are hereby incorporated by reference in their entirety.

What is claimed is:

1. A method for reducing or preventing metastasis of a pancreatic ductal adenocarcinoma in a subject, the method comprising administering to the subject a therapeutically effective amount of the anti-connective tissue growth factor (CTGF) antibody CLN-1 or a fragment thereof that specifically binds to CTGF and a therapeutically effective amount of a cytotoxic chemotherapeutic compound such that the metastasis of the pancreatic ductal adenocarcinoma is reduced or prevented.

2. The method of claim 1, wherein said reduced or prevented metastasis is metastasis to the bone, liver, lymphatic system or peritoneum.

3. The method of claim 1, wherein said method reduces the number or density of tumor blood vessels in the pancreatic ductal adenocarcinoma.

* * * * *